US00PP13151P2

(12) United States Plant Patent
Heims

(10) Patent No.: US PP13,151 P2
(45) Date of Patent: Oct. 29, 2002

(54) HEUCHERA PLANT NAMED 'FLORIST'S CHOICE'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,582

(22) Filed: Jun. 28, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Heuchera plant characterized by its distinctive rose pink flowers, profuse bloom stalks, and reblooming habit.

1 Drawing Sheet

BOTANICAL CLASSIFICATION

Heuchera hybrid.

VARIETY DENOMINATION

'Florist's choice'.

The present invention relates to a new and distinct hybrid of Heuchera, of the family Saxifragaceae, which originated from a cross between unknown parents. This new Heuchera was selected from seedlings grown from select plants that were open pollinated in the field in Canby, Oreg. Given its characteristics we know that *Heuchera sanguinea* and *Heuchera cylindrica* are in its parentage.

This new Heuchera is distinguished by:

1. Tall inflorescences with strong stems.
2. Large, coral pink flowers.
3. Profuse number of inflorescences.

The new variety has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Heuchera 'Florist's Choice' growing in the garden in Canby, Oreg.

DETAILED PLANT DESCRIPTION

The following is a detailed description of the new Heuchera hybrid based on observations of one year old specimens grown in one gallon containers in a cool greenhouse in Canby, Oreg. The color descriptions are all based on The Royal Horticultural Society Colour Chart.

Plant:

*Form.*—Basal rosette, herbaceous perennial.
*Hardiness.*—USDA Zone 5 to 9.
*Size.*—15 cm tall and 23 cm wide.

Leaf:

*Type.*—Simple.
*Arrangement.*—Rosette.
*Shape.*—Orbicular to ovate.
*Lobing/division.*—5 to 7 shallow rounded lobes.
*Venation.*—Palmate.
*Margins.*—Crenate.
*Apex.*—Mucronulate.
*Base.*—Cordate, lobes overlapping.
*Size.*—Grows to 5.5 cm long and 5.2 cm wide.
*Texture.*—Glandular pulverulent.
*Petiole length.*—Grows to 8 cm. at the longest.
*Petiole texture.*—Hirsute.
*Petiole color.*—On young leaf Greyed Red 182B to Yellow Green 146D on older leaf.
*Leaf color.*—Full size young leaves — Closest to 137A. Mature leaves — Between 137A and 147A.

Inflorescence:

*Type.*—Thyrse.
*Number of flowers.*—About 100 per thyrse.
*Peduncle.*—With 0 to 1 bract per scape. Height — about 81 cm. Diameter — 1.75 cm. Color — Greyed Orange 177A. Texture — Hirsute.
*First branch length.*—Grows to 2.3 cm.
*Pedicel.*—Length — 0.4 cm at the longest. Texture — Puberulent. Color — Greyed Orange 177A.
*Bloom period.*—Late spring for about 1½ months.

Flower bud:

*Size.*—0.5 cm.
*Description.*—Glandular pulverulent, downfacing, campanulate when opening.
*Color.*—Red Group 47A.

Flower:

*Type.*—Perfect, zygomorphic, sepals petaloid.
*Sepal shape.*—Campanulate.
*Sepal size.*—0.8 cm long and 0.5 cm wide.
*Sepal color.*—Red 48A outside on lobes and lighter red 49 A–B on rest, Red 48B inside.
*Petal count.*—5, inconspicuous.
*Petal color.*—White 155B.
*Petal shape.*—Elliptic with a clawed base.
*Petal size.*—About 0.2 cm long.
*Calyx.*—Petaloid, divided ½ way to the base, with glandular hairs.
*Sepal number.*—5 lobes.

*Stamen number*.—5.
*Pistil color*.—Yellow Green 145B.
*Pollen color*.—Orange 28 A.
*Fragrance*.—None.
*Lastingness*.—Each thryse blooms for about 2 weeks on the plant.

Fruit:
*Type*.—Two-beaked ovoid capsule.
*Fertility*.—Low.
*Color*.—Tan. RHS 160C Greyed-Yellow to 199C Grey-Brown.

Seed:
*Shape*.—Linear.
*Size*.—2 mm. long.
*Color*.—Black. RHS 202A.

Disease tolerance: Excellent disease resistance to powdery mildew, the common problem of Heuchera.

COMPARISON TO SIMILAR HEUCHERAS

Compared to Heuchera 'Veil of Passion' (U.S. Plant patent application Ser. No. 09/452,026), Heuchera 'Florist's Choice' has more flowers stalks, stronger reblooming, and is less veiled.

Compared to Heuchera 'Palace Passion' (unpatented), Heuchera 'Florist's Choice' is earlier and longer blooming and has more flower stalks per plant. Heuchera 'Palace Passion' also is more veiled and has overlapping leaf bases unlike the new plant.

I claim:

1. A new and distinct hybrid of Heuchera plant substantially as shown and described, characterized by rose pink flowers, profuse flower stalk number and reblooming.

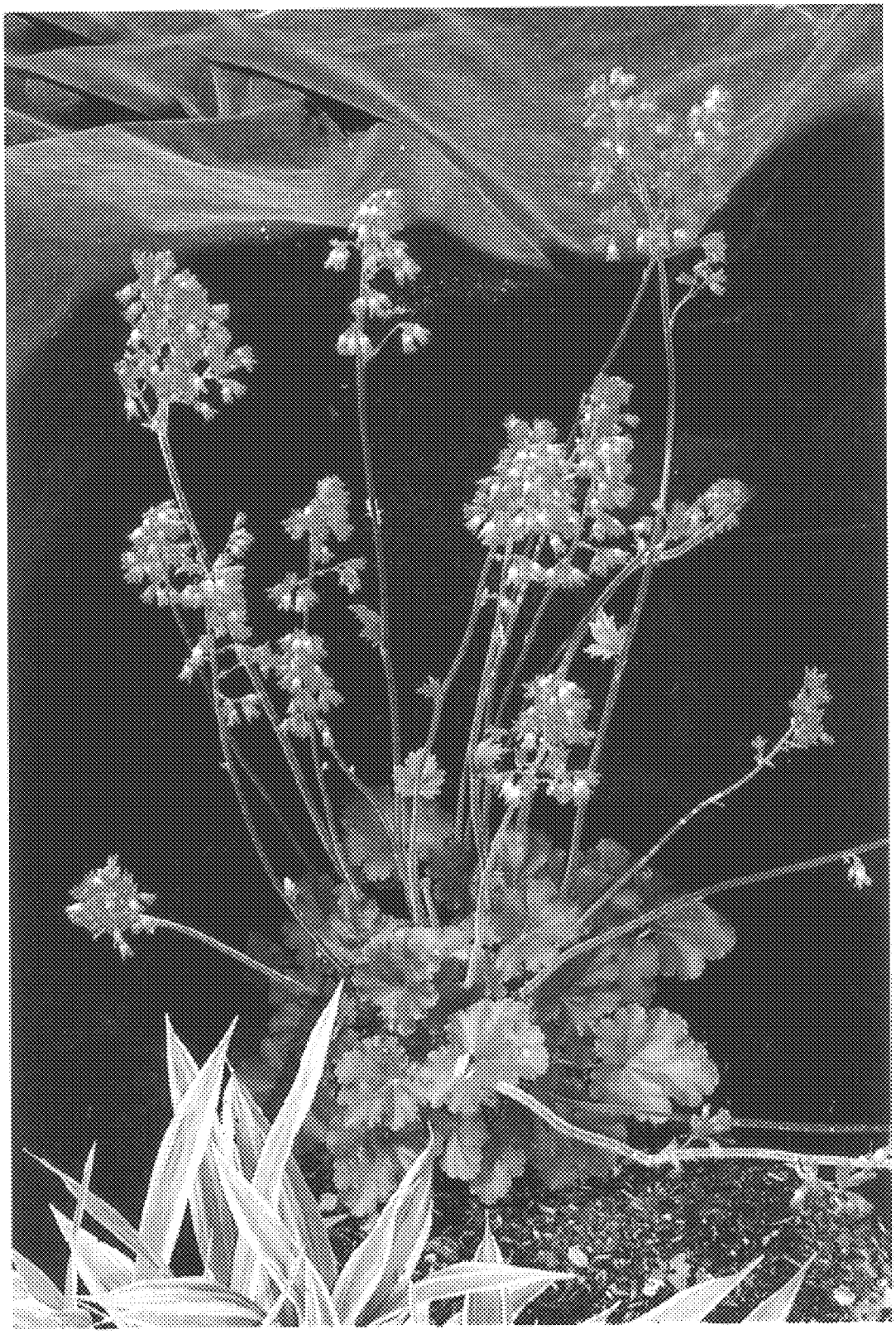

* * * * *